United States Patent
Jiang et al.

(10) Patent No.: US 9,289,531 B2
(45) Date of Patent: Mar. 22, 2016

(54) SOFT ACRYLIC MATERIALS WITH HIGH REFRACTIVE INDEX AND MINIMIZED GLISTENING

(71) Applicant: Novartis AG, Basel (CH)

(72) Inventors: Xuwei Jiang, Arlington, TX (US);
Douglas Schlueter, Azle, TX (US);
Walter Laredo, Fort Worth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/557,704

(22) Filed: Dec. 2, 2014

(65) Prior Publication Data

US 2015/0151022 A1    Jun. 4, 2015

Related U.S. Application Data

(60) Provisional application No. 61/911,547, filed on Dec. 4, 2013.

(51) Int. Cl.
| A61F 2/16 | (2006.01) |
| A61L 27/16 | (2006.01) |
| A61L 27/50 | (2006.01) |
| A61L 27/18 | (2006.01) |
| C08F 220/30 | (2006.01) |
| C08F 220/28 | (2006.01) |
| C08F 236/02 | (2006.01) |
| A61F 2/14 | (2006.01) |

(52) U.S. Cl.
CPC ........... *A61L 27/16* (2013.01); *A61L 27/18* (2013.01); *A61L 27/50* (2013.01); *A61F 2/14* (2013.01); *A61L 2430/16* (2013.01); *C08F 220/30* (2013.01); *C08F 236/02* (2013.01); *C08F 2220/286* (2013.01)

(58) Field of Classification Search
None
See application file for complete search history.

(56) References Cited

U.S. PATENT DOCUMENTS

| 3,162,676 A | 12/1964 | Goldberg |
| 3,299,173 A | 1/1967 | Roselli |
| 4,304,895 A | 12/1981 | Loshaek |
| 4,528,311 A | 7/1985 | Beard |
| 4,612,358 A | 9/1986 | Besecke |
| 4,716,234 A | 12/1987 | Dunks |
| 4,834,750 A * | 5/1989 | Gupta ............... 623/6.58 |
| 5,021,543 A | 6/1991 | Mayska |
| 5,290,892 A | 3/1994 | Namdaran |
| 5,331,073 A | 7/1994 | Weinschenk, III |
| 5,470,932 A | 11/1995 | Jinkerson |
| 5,693,095 A | 12/1997 | Freeman |
| 5,922,821 A | 7/1999 | LeBoeuf |
| 6,241,766 B1 | 6/2001 | Liao |
| 6,245,106 B1 | 6/2001 | Makker |
| 6,313,187 B2 | 11/2001 | LeBoeuf |
| 6,329,485 B1 | 12/2001 | Vanderbilt |
| 6,353,069 B1 | 3/2002 | Freeman |
| 6,528,602 B1 | 3/2003 | Freeman |
| 6,653,422 B2 | 11/2003 | Freeman |
| 6,703,466 B1 | 3/2004 | Karakelle |
| 6,780,899 B2 | 8/2004 | Liao |
| 6,806,337 B2 | 10/2004 | Schlueter |
| 6,872,793 B1 | 3/2005 | Schlueter |
| 7,585,900 B2 | 9/2009 | Cordova |
| 7,605,190 B2 | 10/2009 | Moszner |
| 7,652,076 B2 | 1/2010 | Schlueter |
| 7,714,039 B2 | 5/2010 | Cordova |
| 7,790,824 B2 | 9/2010 | Freeman |
| 7,790,825 B2 | 9/2010 | Lehman |
| 7,799,845 B2 | 9/2010 | Schlueter |
| 7,847,046 B2 | 12/2010 | Schlueter |
| 8,058,323 B2 | 11/2011 | Cordova |
| 8,153,703 B2 | 4/2012 | Laredo |
| 8,232,326 B2 | 7/2012 | Laredo |
| 8,362,177 B1 | 1/2013 | Lehman |
| 8,449,610 B2 | 5/2013 | Laredo |
| 8,466,209 B2 | 6/2013 | Akinay |
| 8,557,892 B2 | 10/2013 | Laredo |
| 2009/0088493 A1 | 4/2009 | Laredo |
| 2013/0030079 A1 * | 1/2013 | Lehman et al. ............ 523/106 |

FOREIGN PATENT DOCUMENTS

| EP | 1071482 B1 | 10/2001 |
| EP | 1002244 B1 | 2/2003 |
| EP | 1080381 B1 | 7/2005 |
| EP | 1080382 B1 | 7/2009 |
| WO | 9908136 A1 | 2/1999 |
| WO | 9952570 A1 | 10/1999 |
| WO | 9953347 A1 | 10/1999 |
| WO | 9953348 A1 | 10/1999 |
| WO | 0034804 A1 | 6/2000 |

OTHER PUBLICATIONS

"Research of High Refractive and Flexible (Meth)acrylic Polymers for Soft Intraocular Lens by Designing Physical Properties of Polymer" authored by Hwang et al. and published in Choson Minjujuui Inman Konghwaguk Kwahagwon Tongbo (2009), 92(2), 40-42.*
Full written translation of "Research of High Refractive and Flexible (Meth)acrylic Polymers for Soft Intraocular Lens by Designing Physical Properties of Polymer" authored by Hwang et al. and published in Choson Minjujuui Inman Konghwaguk Tongbo (2009), 92(2), 40-42.*
Preparation and Infrared Absorption Spectra of Some Phenyl Ethers, K. J. Sax, et al., published in J. Org. Chem., 1960, vol. 25 (9), pp. 1590-1595.
Research of High Refractive and Flexible (Meth)acrylic Polymers for Soft Intraocular Lens by Designing Physical Properties of Polymer, Hwang et al. and published in Choson Minjujuui Inman Konghwaguk Kwahagwon Tongbo (2009), 92(2), 40-42 (English Abstract).

(Continued)

*Primary Examiner* — Marc Zimmer
(74) *Attorney, Agent, or Firm* — Jian Zhou

(57) ABSTRACT

High refractive index acrylic device materials with reduced glistenings are disclosed. The device materials are particularly suitable for use as ophthalmic or otorhhinolaryngological device materials and comprises a poly(phenyl ether)-containing monomer and/or a poly(phenyl ether)-containing cross-linking agent.

15 Claims, No Drawings

(56) References Cited

OTHER PUBLICATIONS

PCT Written Opinion of the International Searching Authority dated Mar. 11, 2015, International Application No. PCT/US2014/068056 International Filing Date Dec. 2, 2014.

PCT International Search Report dated Mar. 11, 2015, International Application No. PCT/US2014/068056 International Filing Date Dec. 2, 2014.
Alcon Brochure: Not all hydrophobic IOLs are AcrySof IQ IOLs, © 2013 Novartis 1/13 NIQ12407FC, pp. 1-6.

* cited by examiner

SOFT ACRYLIC MATERIALS WITH HIGH REFRACTIVE INDEX AND MINIMIZED GLISTENING

This application claims the benefits under 35 USC §119(e) of U.S. provisional application No. 61/911,547 filed Dec. 4, 2013, incorporated by reference in its entirety.

This invention is directed to ophthalmic and otorhinolaryngological device materials. In particular, this invention relates to soft acrylic materials with high refractive index and minimal or no glistening, which are especially suitable for making intraocular lenses (IOLs).

BACKGROUND OF THE INVENTION

With recent technology developments and advances in microincision cataract surgery, increased emphasis has been placed on developing soft, foldable materials suitable for use in intraocular lenses which can be delivered through sub 2.0 mm incisions.

One class of the currently-known soft, foldable materials suitable for intraocular lenses is soft, hydrophobic acrylic materials, for example, those described in U.S. Pat. Nos. 4,834,750, 5,290,892, 5,331,073, 5,693,095, 5,922,821, 6,241,766, 6,245,106, 6,313,187, 6,353,069, 6,528,602, 6,653,422, 6,703,466, 6,780,899, 6,806,337, 6,872,793, 7,585,900, 7,652,076, 7,714,039, 7,790,824, 7,790,825, 7,799,845, 7,847,046, 8,058,323, 8,362,177, 8,466,209, 8,449,610, 8,557,892 (herein incorporated by references in their entireties). Those reported acrylic materials generally may have mechanical and physical properties (e.g., a glass transition temperature of less than about 37° C., a Young's modulus of less than 60 MPa, relatively-high elongation at break of greater than 100%, low tackiness, etc.) suitable for foldable intraocular lenses. But, they generally have a refractive index higher than 1.50 but lower than 1.56. As such, those known acrylic materials may have limited use as microincision intraocular lenses because of the thicker lens optic necessary to achieve a given refractive power.

However, with increases in the refractive index of a soft hydrophobic acrylic material, glistenings (or microvacuoles) may become more apparent in IOLs made of such a material. Glistenings are tiny inclusions of water present within the matrix of an IOL material and are visible due to differences in refractive indices between the IOL material and water within the IOL material. It is reported that polyethylene glycol (PEG) dimethacrylates and/or PEG mono-(meth)acrylate can be used to improve glistening resistance of hydrophobic acrylic formulations. See, for example, U.S. Pat. Nos. 5,693,095, 6,353,069, and 8,449,610. But, in order to minimize its adverse effects on the refractive index of acrylic materials, low amounts of PEG dimethacrylate or PEG mono-(meth)acrylate concentrations are often required. Addition of PEG dimethacrylates or PEG mono-(meth)acrylates also tends to decrease the modulus and tensile strength of the resulting copolymer.

Therefore, there is a need for a soft hydrophobic acrylic material having a refractive index higher than that of known acrylic materials, glistening resistance, and physical and mechanical properties suitable for making intraocular lenses.

SUMMARY OF THE INVENTION

In accomplishing the foregoing, the present invention provides soft, foldable hydrophobic acrylic device materials which are particularly suited for use as IOLs, but which are also useful as other ophthalmic or otorhinolaryngological devices, such as contact lenses, keratoprostheses, corneal rings or inlays, otological ventilation tubes and nasal implants, have been discovered. These polymeric materials comprise a poly(phenylether)-containing component.

Among other factors, the present invention is partly based on the finding that poly(phenyl ether)-containing monomers can be used in making soft hydrophobic acrylic device materials with a refractive index of from 1.57 to higher than 1.58, higher than those of the currently known acrylic materials. The present invention is also partly based on the discovery that, by combining use of a poly(phenylether)-containing monomer and a molecular weight, reactive, linear polyethylene glycol monomer in acrylic intraocular lens formulations, temperature-induced glistening formation in hydrophobic acrylic copolymers can be efficiently reduced or eliminated. The subject materials are suitable for making glistening resistant, low equilibrium water content, higher refractive index IOLs.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

Unless indicated otherwise, all component amounts are presented on a % (w/w) basis ("wt. %").

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), C$_1$-C$_4$ alkyl, C$_1$-C$_4$ alkoxy, C$_1$-C$_4$ alkylthio (alkyl sulfide), C$_1$-C$_4$ acylamino, C$_1$-C$_4$ alkylamino, di-C$_1$-C$_4$ alkylamino, halogen atom (Br or Cl), and combinations thereof.

In general, the invention is directed to ophthalmic or otorhhinolaryngological device materials which are soft, hydrophobic acrylic materials. A polymeric ophthalmic or otorhhinolaryngological device material of the invention has a refractive index of 1.57 or greater (preferably 1.58 or greater) measured at 589 nm and at room temperature (23±3° C.) in fully hydrated state, a Young's modulus of about 60 MPa or less (preferably from about 1 MPa to about 45 MPa, more preferably from about 2.5 MPa to about 30 MPa, even more preferably from about 5 MPa to 25 MPa), a glass transition temperature of about 35° C. or less (preferably about 30° C. or less, more preferably from about −25° C. to 25° C.), an elongation of at least 100% (preferably at least 110%, more preferably at least 120%, even more preferably at least 130%, most preferably from 130% to 300%), and is obtained from a polymerizable composition comprising a poly(phenyl ether)-containing monomer of formula (IA) and/or a poly (phenyl ether)-containing cross-linking agent of formula (IB)

For use in IOLs, the device materials of the present invention preferably exhibit sufficient strength to allow devices made of them to be folded or manipulated without fracturing. Thus, an ophthalmic device material of the present invention will have an elongation (% strain at break) of at least 100%, preferably at least 130%, and most preferably between 130 and 300%. This property indicates that lenses made of such a material generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions (23±2° C., 50±5% relative humidity) using an Instron Material Tester (Model No. 4442 or equivalent) with a 50 Newton load cell. The grip distance is

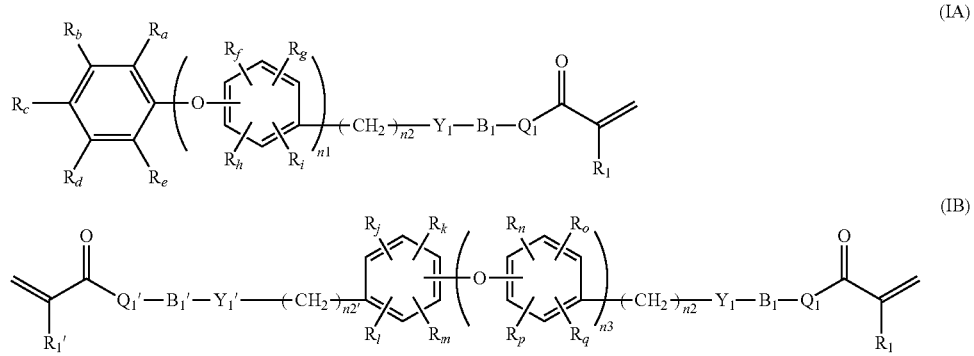

wherein:
  $R_1$ and $R_1'$ independently of each other are H or $CH_3$;
  $R_a, R_b, R_c, R_d, R_e, R_f, R_g, R_h, R_i, R_j, R_k, R_l, R_m, R_n, R_o, R_p,$ and $R_q$ independent of one another are H, $C_1$-$C_{12}$ alkyl, or $C_1$-$C_{12}$ alkoxy (preferably all are H);
  $B_1$ and $B_1'$ independently of each other are a direct bond, $(CH_2)_{m1}$, or $(OCH_2CH_2)_{m2}$, in which m1 is 2-6 and m2 is 1-10;
  $Q_1$ and $Q_1'$ independently of each other are a direct bond, O, NH, or C(=O)NH$(CH_2)_{m3}$O in which m3 is an integer of 2-6;
  n1 is an integer from 1 to 9 (preferably from 2 to 6, more preferably from 2 to 4, even more preferably 2 or 3);
  n2 and n2' independently of each other are an integer from 0 to 6 (preferably from 0 to 4);
  n3 is an integer from 1 to 100 (preferably from 5 to 75, more preferably from 20 to 60); and
  $Y_1$ and $Y_1'$ independently of each other are a direct bond, O, S, OC(=O)NH, NHC(=O)NH, or NR' in which R' is H, $C_1$-$C_{10}$ alkyl, $C_6H_5$, or $CH_2C_6H_5$.

For use in IOLs, a device material of the invention should not have a glass transition temperature (Tg) greater than 37° C., which is normal human body temperature. Materials having glass transition temperatures higher than 37° C. are not suitable for use in foldable IOLs; such lenses could only be rolled or folded at temperatures above 37° C. and would not unroll or unfold at normal body temperature. An ophthalmic device material of the invention preferably has a glass transition temperature of about 30° C. or less, more preferably from about −25° C. to 25° C., so that the material can be rolled or folded conveniently at room temperature. Tg is measured by differential scanning calorimetry at 10° C./minute, and is determined at the midpoint of the transition of the heat flux curve.

set at 14 mm and a crosshead speed is set at 500 mm/minute and the sample is pulled until failure. The elongation (strain) is reported as a fraction of the displacement at failure to the original grip distance. The strain at break is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 25% secant modulus is calculated as the slope of a straight line drawn on the stress-strain curve between 0% strain and 25% strain. The 100% secant modulus is calculated as the slope of a straight line drawn on the stress-strain curve between 0% strain and 100% strain. Since materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test is begun.

For IOL applications, the stiffness of the device material must be low enough to permit folding and injection through a small diameter opening (e.g., 1-3 mm) without tearing or deforming after injection. In a preferred embodiment, the Young's Modulus of the device material will be about 60 MPa or less (preferably from about 1 MPa to about 45 MPa, more preferably from about 2.5 MPa to about 30 MPa, even more preferably from about 5 MPa to 25 MPa.

A device material of the present invention preferably further has an equilibrium water content of less than 2.0 weight % (preferably about 1.6% or less, more preferably about 1.2% or less, even more preferably about 1.0% or less) across the temperature range of 16-45° C. and preferably less than 2.5 weight % in the temperature range of 16-23° C. The device materials are preferably resistant to glistenings such that when equilibrated in water at 45° C. and subsequently allowed to cool to ambient temperature (approximately 22° C.) should produce very few to no microvacuoles as detected by microscopic examination.

Poly(phenyl ether)-containing monomers of formula (IA) can be prepared from monofunctional polyphenyl ethers (i.e., ones with one functional group such as hydroxyl, amino, or carboxyl groups). Generally, a monofunctional OH-terminated poly(phenyl ether) is reacted with a (meth)acrylic acid derivative (such as acryloyl chloride, methacryloyl chloride, methacrylic anhydride, or an isocyanatoalkyl acrylate or methacrylate) under coupling reaction conditions known to a person skilled in the art. Mono-amine and mono-carboxylic acid terminated polyphenyl ethers are functionalized in a similar manner using suitable (meth)acrylic acid derivatives. Monofunctional terminated polyphenyl ethers can be prepared according to procedures described in literature (*J. Org. Chem.*, 1960, 25 (9), pp 1590-1595, herein incorporated by reference in its entirety).

Poly(phenyl ether)-containing cross-linking agent of formula (IB) can be prepared from bifunctional terminated polyphenyl ethers (i.e., ones with two terminal functional groups, e.g., hydroxyl, amino, or carboxyl groups). Generally, a bifunctional OH-terminated poly(phenyl ether) is reacted with a (meth)acrylic acid derivative (such as acryloyl chloride, methacryloyl chloride, methacrylic anhydride, or an isocyanatoalkyl acrylate or methacrylate) under reaction conditions known to a person skilled in the art. Bifunctional amine- and carboxylic acid-terminated polyphenyl ethers are functionalized in a similar manner using suitable (meth) acrylic acid derivatives. Bifunctional terminated polyphenyl ethers can be prepared according to procedures described in U.S. Pat. No. 5,021,543 (herein incorporated by reference in its entirety).

In a preferred embodiment, the poly(phenyl ether)-containing monomer in the polymerizable composition is represented by formula (IA) in which n1 is 2 or 3. Examples of such preferred poly(phenyl ether)-containing monomers include without limitation:

In a preferred embodiment, the polymerizable composition for making an ophthalmic device material of the invention comprises: a) from about 40% to about 95% by weight (preferably from about 45% to about 85% by weight, more preferably from about 50% to about 75% by weight) of at least one poly(phenyl ether)-containing monomer of formula (IA) as defined above and b) from about 1% to about 6% by weight (preferably from about 2% to about 5% by weight) of a poly(ethylene glycol)-containing polymerizable component comprising at least one polymerizable group which is acryloyl (OC(=O)CH=CH$_2$), methacryloyl (OC(=O)CCH$_3$=CH$_2$), acrylamido (NHC(=O)CH=CH$_2$), methacrylamido (NHC(=O)CCH$_3$=CH$_2$), or thiol group, preferably is acryloyl, methacryloyl, acrylamido, or methacrylamido group, more preferably is acryloyl or methacryloyl, even more preferably is acryloyl group. It is understood that the weight percentages are based on the total amount of polymerizable components in the polymerizable composition.

In accordance with the invention, a poly(ethylene glycol)-containing polymerizable component can be a linear poly(ethylene glycol) with one or two terminal polymerizable groups as described above, or a branched poly(ethylene glycol) with three or more terminal polymerizable groups as described above. Such a poly(ethylene glycol)-containing polymerizable component can be prepared according to methods known in the art from commercially available polyethylene glycols with one or more terminal functional groups (e.g., hydroxyl, amino, or carboxyl groups). Generally, a poly(ethylene glycol) with one or more hydroxyl terminal groups is dissolved in tetrahydrofuran and treated with a (meth) acrylic acid derivative such as methacryloyl chloride or methacrylic anhydride in the presence of triethylamine or pyridine. The reaction proceeds until greater than 90% of the hydroxyl groups have been converted to the corresponding acrylic or methacrylic esters. The polymer solution is filtered and the polymer is isolated by precipitation into diethyl ether. Amine and carboxylic acid terminated polyethylene glycols are functionalized in a similar manner using suitable (meth) acrylic acid derivatives.

Preferably, the poly(ethylene glycol)-containing polymerizable component used in the invention is represented by formula (II)

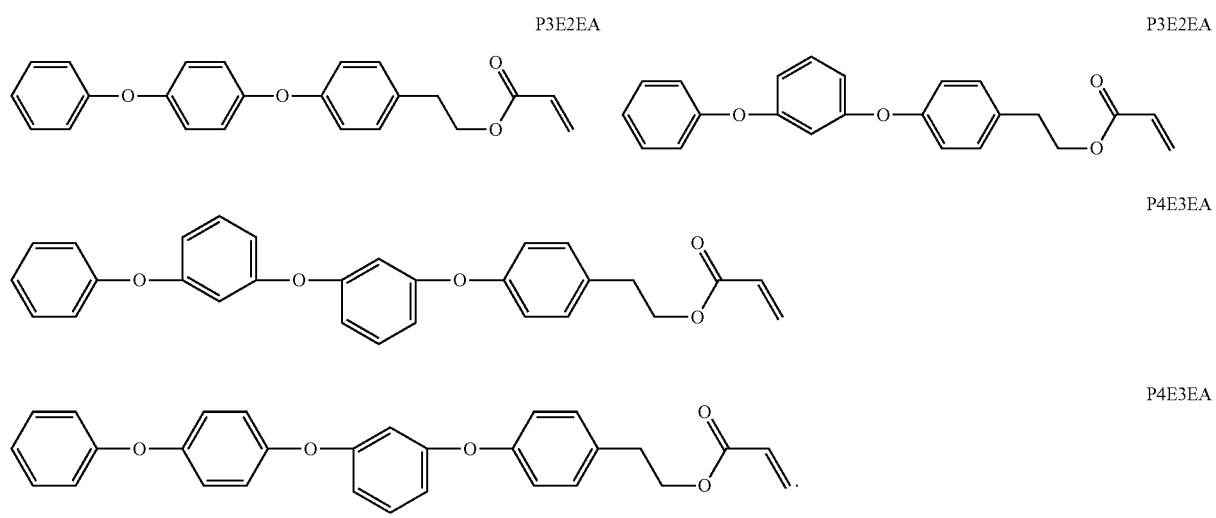

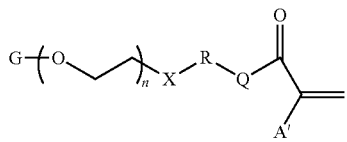

(II)

wherein:
A' is H or CH$_3$;
Q and Q' independently of each other are a direct bond, O, NH, or C(=O)NHCH$_2$CH$_2$O;
X and X' independently are a direct bond, O, NH, OC(=O)NH, or NHC(=O)NH;
R and R' independently of each other are a direct bond, or (CH$_2$)$_p$;
p=1-3;
m=2-6;
G is H, C$_1$-C$_4$ alkyl, (CH$_2$)$_m$NH$_2$, (CH$_2$)$_m$CO$_2$H, or R'-X'-Q'-C(=O)CA'=CH$_2$; and
n=45-225 when G=H, C$_1$-C$_4$ alkyl, (CH$_2$)$_m$NH$_2$, or (CH$_2$)$_m$CO$_2$H; otherwise, n=51-225.

Poly(ethylene glycol)-containing polymerizable components of formula (II) can be made by methods known in the art. For example, they can be prepared according to the procedures described above or as described in U.S. Pat. No. 8,449,610 (herein incorporated by reference in its entirety).

Preferred poly(ethylene glycol)-containing polymerizable components of formula (II) are those wherein: X and X' independently of each other are a direct bond or O; R and R' are a direct bond; Q and Q' independently of each other are a direct bond or C(=O)NHCH$_2$CH$_2$O; A' is H or CH$_3$; G is C$_1$-C$_4$ alkyl or R'-X'-Q'-C(=O)CA'=CH$_2$; and n=45-180 when G=C$_1$-C$_4$ alkyl; otherwise, n=51-225.

Although the total amount of the component of formula (II) contained in the device materials of the present invention is 1-5% by weight, is preferably 2-5% by weight, and is most preferably 2-4% by weight, of the total amount of polymerizable components of the device materials, such amount may comprise one component of formula (II) or combinations of components of formula (II). The component of formula (II) has a number average molecular weight of 2,000-10,000 Daltons, preferably 2,000-8,000 Daltons, more preferably 2,000-6,000 Daltons, and most preferably 2,500-6,000 Daltons.

In another preferred embodiment, the polymerizable composition for making an ophthalmic device material of the invention further comprises from about 10% to about 45% by weight (preferably from about 15% to about 40% by weight, more preferably from about 20% to about 35% by weight) of one or more aryl acrylic monomers of formula (III)

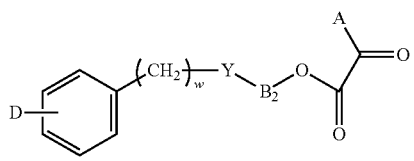

wherein:
A is H or CH$_3$;
B$_2$ is (CH$_2$)$_m$ or [O(CH$_2$)$_2$]$_z$;
m is 2-6;
z is 1-10;
Y is a direct bond, O, S, or NR', provided that if Y is O, S, or NR', then B is (CH$_2$)$_m$;
R' is H, CH$_3$, C$_n$H$_{2n'+1}$, iso-OC$_3$H$_7$, C$_6$H$_5$, or CH$_2$C$_6$H$_5$;
n'=1-10;
w is 0-6, provided that m+w≤8; and
D is H, Cl, Br, C$_1$-C$_4$ alkyl, C$_1$-C$_4$ alkoxy, C$_6$H$_5$, or CH$_2$C$_6$H$_5$.

Monomers of formula (III) can be made by methods known in the art. For example, the conjugate alcohol of the desired monomer can be combined in a reaction vessel with methyl acrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding acrylic acid to the conjugate alcohol and catalyzing with a carbodiimide or mixing the conjugate alcohol with acryloyl chloride and a base such as pyridine or triethylamine.

Suitable monomers of formula (III) include, but are not limited to: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate;
2,4-methylphenylethyl methacrylate; 2-(4-propylphenyl)ethyl acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl)ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; or combinations thereof.

Preferred aryl acrylic monomers of formula (I) are those wherein B$_1$ is (CH$_2$)$_{m1}$, m1 is 2-5, Y$_1$ is nothing or O, w1 is 0 or 1, and D$_1$ is H. Most preferred are 2-phenylethyl acrylate; 3-phenylpropyl acrylate; 4-phenylbutyl acrylate; 5-phenylpentyl acrylate; 2-benzyloxyethyl acrylate; 3-benzyloxypropyl acrylate; 2-[2-(benzyloxy)ethoxy]ethyl acrylate; and their corresponding methacrylates.

The polymerizable composition for making an ophthalmic device material of the invention preferably further comprises a polymerizable cross-linking agent. The cross-linking agent may be any terminally ethylenically unsaturated compound having more than one unsaturated groups. Suitable cross-linking agents include, for example: ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; ethylene glycol diacrylate; diethylene glycol diacrylate; triethylene glycol diacrylate, tetraethylene glycol diacrylate, allyl acrylate; 1,3-propanediol diacrylate; 2,3-propanediol diacrylate; 1,6-hexanediol diacrylate; 1,4-butanediol diacrylate; N,N'-hexamethylene bisacrylamide; N,N'-hexamethylene bismethacrylamide; N,N'-dihydroxyethylene bisacrylamide; N,N'-dihydroxyethylene bismethacrylamide; N,N'-methylene bisacrylamide; N,N'-methylene bismethacrylamide; $CH_2=C(CH_3)C(=O)O-(CH_2CH_2O)_p-C(=O)C(CH_3)=CH_2$ where p=1-50; $CH_2=CHC(=O)O-(CH_2CH_2O)_p-C(=O)CH=CH_2$ where p=1-50; $CH_2=C(CH_3)C(=O)O(CH_2)_tO-C(=O)C(CH_3)=CH_2$ where t=3-20; and $CH_2=CHC(=O)O(CH_2)_tO-C(=O)CH=CH_2$ where t=3-20. A preferred cross-linking monomer is $CH_2=C(CH_3)C(=O)O-(CH_2CH_2O)_p-C(=O)C-(CH_3)=CH_2$ where p is such that the number-average molecular weight is about 400, about 600, or about 1000. Other preferred cross-linking monomers are ethylene glycol dimethacrylate (EGDMA), diethylene glycol dimethacrylate, triethylene glycol dimethacrylate, triethylene glycol diacrylate, and 1,4-butanediol diacrylate (BDDA).

Generally, the total amount of the cross-linking component is at least 0.1% by weight and, depending on the identity and concentration of the remaining components and the desired physical properties, can range to about 20% by weight. The preferred concentration range for the cross-linking component is 1-5% for small, hydrophobic compounds with molecular weights typically less than 500 Daltons, and 5-17% (w/w) for larger, hydrophilic compounds.

In addition to one or more monomers of formula (I), one or more monomers of formula (II), one or more monomers of formula (III), and one or more cross-linking agents, the ophthalmic device materials of the present invention may also contain other ingredients, including, but not limited to, polymerizable UV-absorbers (or UV-absorbing agents), polymerizable colored dyes, additives to reduce tack, siloxane monomers, and combinations thereof.

A polymerizable ultraviolet (UV) absorbing agent can also be included in the materials of the present invention. The polymerizable UV-absorbing agent can be any compound which absorbs UV light (i.e., light having a wavelength shorter than about 380 nm) and optionally high-energy-violet-light (HEVL) (i.e., light having a wavelength between 380 nm and 440 nm), but does not absorb any substantial amount of visible light having a wavelength greater than 440 nm. The UV-absorbing compound is incorporated into the monomer mixture and is entrapped in the polymer matrix when the monomer mixture is polymerized. Any suitable polymerizable UV-absorbing agents can be used in the invention. A polymerizable UV-absorbing agent used in the invention comprises a benzophenone-moiety or preferably a benzotriazole-moiety. Polymerizable benzophenone-containing UV-absorbing agents can be prepared according to procedures described in U.S. Pat. Nos. 3,162,676 and 4,304,895 (herein incorporated by reference in their entirety) or can be obtained from commercial suppliers. Polymerizable benzotriazole-containing UV-absorbing agents can be prepared according to procedures described in U.S. Pat. Nos. 3,299,173, 4,612,358, 4,716,234, 4,528,311, 8,153,703, and 8,232,326 (herein incorporated by reference in their entireties) or can be obtained from commercial suppliers.

Examples of preferred polymerizable benzophenone-containing UV-absorbing agents include without limitation 2-hydroxy-4-acryloxy alkoxy benzophenone, 2-hydroxy-4-methacryloxy alkoxy benzophenone, allyl-2-hydroxybenzophenone, 4-acryloylethoxy-2-hydroxybenzophenone (UV2), 2-hydroxy-4-methacryloyloxybenzophenone (UV7), or combinations thereof.

Examples of preferred polymerizable benzotriazole-containing UV-absorbing and UV/HEVL-absorbing agents include without limitation: 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl) benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxypropylphenyl) benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl)benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5'[3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl-(UVAM), 2-(2'-hydroxy-5'-methacryloxyethylphenyl) benzotriazole (2-Propenoic acid, 2-methyl-, 2-[3-(2H-benzotriazol-2-yl)-4-hydroxyphenyl]ethyl ester, Norbloc), 2-{2'-Hydroxy-3'-tert-butyl-5'-[3'-methacryloyloxypropoxy]phenyl}-5-methoxy-2H-benzotriazole (UV13), 2-[2'-Hydroxy-3'-tert-butyl-5'-(3'-acryloyloxypropoxy)phenyl]-5-trifluoromethyl-2H-benzotriazole ($CF_3$-UV13), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methylphenyl)-2H-benzotriazole (UV12), 2-3'-t-butyl-2'-hydroxy-5'-(3"-dimethylvinylsilylpropoxy)-2'-hydroxy-phenyl)-5-methoxybenzotriazole (UV15), 2-(2'-hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS#96478-15-8), 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9CI) (CAS#83063-87-0).

More preferably, a polymerizable UV-absorbing agent is 2-(2H-benzo[d][1,2,3]triazol-2-yl)-4-methyl-6-(2-methylallyl)phenol (oNTP), 3-[3-tert-butyl-4-hydroxy-5-(5-methoxy-2-benz[d][1,2,3]triazol-2-yl)phenoxy]propyl methacrylate (UV13), and 2-[3-(2H-benzotriazol-2-yl)-4-hydroxyphenyl]ethyl methacrylate (Norbloc 7966), or combinations thereof.

In addition to ultraviolet absorbing materials, ophthalmic devices made of the copolymers of the present invention may include colored dyes, such as the yellow dyes disclosed in U.S. Pat. No. 5,470,932.

The device materials of the present invention may also contain additives to reduce or eliminate tack. Examples of such additives include those disclosed in U.S. Pat. Nos. 7,585,900 and 7,714,039, the entire contents of which are incorporated by reference herein.

In one embodiment, the device materials of the present invention also contain a siloxane monomer of formula (IV)

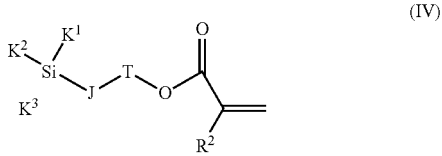

(IV)

wherein
R$^2$ is H or CH$_3$;
T is a direct bond, O(CH$_2$)$_b$, or OCH$_2$CH(OH)CH$_2$;
b is 1-3;
J is (CH$_2$)$_z$; and
K$^1$, K$^2$, and K$^3$ independently are CH$_3$, C$_6$H$_5$, or OSi(CH$_3$)$_3$.

Monomers of formula (IV) may be made by known methods and in some cases are commercially available. Preferred monomers of formula (IV) are those wherein R$^2$ is CH$_3$, T is a direct bond or OCH$_2$CH(OH)CH$_2$, J is (CH$_2$)$_3$, and K$^1$, K$^2$, and K$^3$ independently are CH$_3$, C$_6$H$_5$, or OSi(CH$_3$)$_3$.

Most preferred monomers of formula (IV) are those selected from the group consisting of: 3-[tris(trimethylsilyloxy)silyl]-propyl methacrylate ("TRIS"); 3-(methacryloxy-2-hydroxypropoxy)propylmethylbis(trimethoxy)silane (SiMA); methacryloxypropylpentamethyldisiloxane; 3-methacryloxypropylbis(trimethylsiloxy)methylsilane; methacryloxymethyltris(trimethylsiloxy)silane; (methacryloxymethyl)phenyl-dimethylsilane; and (methacryloxymethyl)bis(trimethylsiloxy)methylsilane.

The amount of monomer of formula (IV) in the materials of the present invention will range from 5-30%, preferably 5-25%, and most preferably 5-15%.

The copolymers of this invention are prepared by conventional polymerization methods. For example, a mixture of the liquid monomers of formula (I)-(III), and a cross-linking agent in the desired proportions, together with any other polymerizable components, such as a UV absorber, yellow dye, and/or additive to reduce tack, and a conventional thermal free-radical initiator is prepared. The mixture can then be introduced into a mold of desired shape, and the polymerization carried out thermally (i.e., by heating) or photochemically (i.e., by actinic radiation, e.g., UV radiation and/or visible radiation) to activate the initiator.

Examples of suitable thermal initiators include: but are not limited to, azonitriles, such as 2,2'-azobis (2,4-dimethylpentanenitrile), 2,2'-azobis (2-methylpropanenitrile), 2,2'-azobis (2-methylbutanenitrile), 2,2'-azobis(isobutyronitrile) (AIBN); peroxides, such as benzoyl peroxide; peroxycarbonates, such as bis-(4-t-butylcyclohexyl) peroxydicarbonate, and the like. A preferred initiator is AIBN.

Where the polymerization is carried out photochemically, a mold should be transparent to actinic radiation of a wavelength capable of initiating polymerization. Conventional photoinitiator compounds, e.g., a benzophenone-type or bisa-cylphosphine oxide (BAPO) photoinitiator, can also be introduced to facilitate the polymerization. Suitable photoinitiators are benzoin methyl ether, diethoxyacetophenone, a benzoylphosphine oxide, 1-hydroxycyclohexyl phenyl ketone, Darocur and Irgacur types photoinitiators (preferably Darocur 1173®, Darocur 2959® and Irgacure 819®), and Germane-based Norrish Type I photoinitiators which are capable of initiating a free-radical polymerization under irradiation with a light source including a light in the region of about 400 to about 550 nm. Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Examples of Germane-based Norrish Type I photoinitiators are acylgermanium compounds described in U.S. Pat. No. 7,605,190 (herein incorporated by reference in its entirety).

Regardless of the chosen initiator or curing method, the curing process should be controlled to avoid rapid polymerization, which may yield polymerized materials having more tack than the same materials polymerized more slowly.

Once the ophthalmic device materials of the present invention have been cured, they are extracted in a suitable solvent to remove as much of the unreacted components of the materials as possible. Examples of suitable solvents include acetone, methanol, and cyclohexane. A preferred solvent for extraction is acetone.

IOLs constructed of the disclosed ophthalmic device materials can be of any design capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are attached to the optic and are like arms which hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the ophthalmic device materials of the present invention are also suitable for use in other devices, including contact lenses, keratoprostheses, intracorneal lenses, corneal inlays or rings, and glaucoma filtration devices.

These device materials can be used to form intraocular lenses with low surface tack and high refractive indexes. Lenses made of these materials are flexible and transparent, can be inserted into the eye through a relatively small incision, and recover their original shape after having been inserted.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

EXAMPLE 1

Synthesis of
2-[4-(4-phenoxyphenoxy)phenyl]ethanol

To a 1 L round bottom flask were charged 4-phenoxyphenol (95.0 g, 0.51 mol). THF (100 mL), sodium hydroxide (24 g, 0.6 mol), and DI water (80 mL). The mixture was magnetically stirred at room temperature for 30 minutes, followed by removal of solvent under reduced pressure. The white solid was then dried under vacuum (70 mTorr) at 150° C. overnight and cooled to room temperature. To the flask were then added 1-bromo-4-[2-(phenylmethoxy)ethyl]benzene (150 g, 0.51 mol) and anhydrous pyridine (100 mL). The mixture was purged with nitrogen for 15 minutes, followed by the addition of cuprous chloride (5 g, 0.05 mol). The mixture was then purge with nitrogen for additional 15 min and then sealed under nitrogen and magnetically stirred in a 130° C. oil bath for a week. After removal of pyridine under vacuum, the crude product was dissolved in methylene chloride (600 mL) and washed with 2N HCl (200 mL×3), 2N NaOH (200 mL×3). After removal of solvent under reduced pressure, the crude product was recrystallized from methanol/ethyl acetate (9/1, v/v). The product was then hydrogenated at 100 PSI in THF using palladium 10% on carbon as catalyst to give crude 2-[4-(4-phenoxyphenoxy)phenyl]ethanol. This crude product was then distilled under vacuum followed by recrystallization from hexanes/ethyl acetate (1/1, v/v) to give the product as white crystals (122 g, 78% over two steps).

Synthesis of 2-[4-(4-phenoxyphenoxy)phenyl)ethyl acrylate (P3E2EA)

To a 1 L three-neck round bottom flask equipped with mechanical stirrer were charged 2-[4-(4-phenoxyphenoxy) phenyl]ethanol (61.2 g, 0.2 mol), anhydrous triethylamine (60 mL, 0.42 mol), and anhydrous methylene chloride (300 mL). The solution was cooled in an ice/salt bath under dry air blanket for 15 mins. Acryloyl chloride (22 mL, 0.27 mol) was added into the vigorously stirred cold solution through an addition funnel over 60 min and the addition rate was adjusted to keep the temperature of the reaction mixture below 10° C. After the addition, the reaction mixture was stirred in the ice/salt bath for additional two hours followed by quenching with the addition of 2M HCl (300 mL). The mixture was extracted with ethyl acetate (300 mL×3) and the combined organic layer was washed with DI water (200 mL×3), aqueous sodium bicarbonate (200 mL×2), and dried over $MgSO_4$. Filtration and removal of solvents under reduced pressure gave the crude product as light brown oil which was purified on silica gel using Hexanes/Ethyl acetate (9/1, v/v) as eluent to give P3E2EA as a white powder (62 g, 86%).

EXAMPLE 2

Synthesis of 2-[2-(Benzyloxy)ethoxy]ethyl acrylate (DEGMBA)

To a 1 L three-neck round bottom flask equipped with mechanical stirrer were charged diethylene glycol monobenzyl ether (98.0 g, 0.5 mol), anhydrous triethylamine (120 mL, 0.85 mol), and anhydrous THF (300 mL). The solution was cooled in an ice/salt bath under dry air blanket for 15 minutes. Acryloyl chloride (55 mL, 0.68 mol) was added into the vigorously stirred cold solution through an addition funnel over 90 minutes and the addition rate was adjusted to keep the temperature of the reaction mixture below 10° C. After the addition, the reaction mixture was stirred in the ice/salt bath for additional two hours followed by quenching with the addition of 2M HCl (400 mL). The mixture was extracted with ethyl acetate (300 mL×3) and the combined organic layer was washed with DI water (200 mL×3), aqueous sodium bicarbonate (200 mL×2), and dried over $MgSO_4$. Filtration and removal of solvents under reduced pressure gave the crude product as light brown oil which was purified on silica gel using Hexanes/Ethyl acetate (4/1, v/v) as eluent to give the final product as a colorless oil (105.0 g, 0.42 mol, yield: 84%).

EXAMPLE 3

Crosslinked Polymers

The monomers from Examples 1 and 2 were formulated as shown in Table 1. Test samples measuring 0.9 mm in thickness were blue light cured at 55° C. for 1 hour. Samples were extracted in acetone for 20 hours at 55° C. and then dried slowly at ambient temperature for 20 hours, followed by vacuum (0.1 mm Hg) for a minimum of 20 hours at 70° C.

TABLE 1

| Component | EXAMPLE (% w/w) | | |
|---|---|---|---|
| | 44B | 44E | 54C |
| P3E2EA | 51.45 | 66.66 | — |
| P4E3EA | — | — | 66.66 |
| DEGMBA | 45.20 | 25.00 | 24.99 |
| PolyPEGMA | — | 4.99 | 5.00 |
| BDDA | 1.55 | 1.50 | 1.51 |
| oMTP | 1.76 | 1.80 | 1.80 |
| Blue Blocker | 0.04 | 0.04 | 0.04 |
| Irgacure 819 | 0.21 | 0.30 | 0.32 |

PTEA = 2-(phenylthio)ethyl acrylate
PTEMA = 2-(phenylthio)ethyl methacrylate
BDDA = 1,4-butanediol diacrylate
polyPEGMA = methacrylate terminated polymer with Mn = 3,900 derived from PEG (350) monomethyl ether methacrylate
oMTP = 2-(2H-benzo[d][1,2,3]triazol-2-yl)-4-methyl-6-(2-methylallyl)phenol
Blue blocker = N-[2-[4-hydroxy-3-[2-(2-methylphenyl)diazenyl]phenyl]ethyl]methacryamide
Irgacure 819 = phenylbis (2,4,6-trimethylbenzoyl)phosphine oxide The samples prepared above were hydrated in a waterbath at 23° C. and the % EWC (equilibrium water content) and refractive index were determined at 23° C. The results are reported in Table 2.

The tensile properties of the samples prepared above were also evaluated as follows. Tensile bar specimens in the fashion of "dogbones" were cut from each sample group using a die and press. Typically 3 specimens per slab were prepared and 9 total specimens per formulation. Tensile properties were measured using an Instron 5543 extensometer at 500 mm/min crosshead speed. Stress at break, % strain at break, Young's modulus, and 100% secant modulus data were obtained. The results are shown in Table 2.

Glistening resistance was determined by placing three lenses of each formulation into 20-mL vials containing about 20 mL deionized water and incubating them in a waterbath at 45° C. for 24 hours. The sample vials were removed from the water bath and placed on the lab bench to cool to room temperature (typically 23-24° C.). After cooling to room temperature, each lens was imaged using an Olympus BX60 microscope under bright field (BF) and dark field (DFA) settings at 10 times with a 2 times magnifier.

The weight percentage of extractables was determined as follows. Three-five polymer slabs of each cured formulation were weighed for % extractables. The polymer slabs were extracted in acetone for at least 16 hours at ambient temperature with one solvent change out after the first hour, and then allowed to dry while covered with aluminum foil at ambient temperature for 8 hours. Slabs were further dried under reduced atmosphere at 60° C. for at least 16 hours. Slabs were removed and cooled to room temperature (23° C.). Previously weighed slabs were weighed again for % extractables. The results are reported in Table 2.

TABLE 2

| Sample ID | % Extractables (N = 12) | EWC (%) | R.I. at 589 nm (hydrated) | Young's Modulus (MPa) | Strain at Break (%) | 100% Secant Modulus (MPa) |
|---|---|---|---|---|---|---|
| 44B | 2.9 | 0.6 | 1.574 | — | — | — |
| 44E | 4.7 | 1.6 | 1.582 | 22.3 | 128 | 1.7 |
| 54C | 3.3 | 1.4 | 1.587 | 25.6 | 125 | 1.9 |

We claim:

1. A polymeric ophthalmic or otorhhinolaryngological device material, having a refractive index of 1.57 or greater measured at 589 nm and at room temperature (23±3° C.) in fully hydrated state, a Young's modulus of about 60 MPa or less, a glass transition temperature of about 35° C. or less, an elongation of at least 100%, wherein the polymeric ophthalmic or otorhhinolaryngological device material is a copolymerization product of a polymerizable composition comprising a poly(phenyl ether)-containing monomer of formula (IA) and/or a poly(phenyl ether)-containing cross-linking agent of formula (IB)

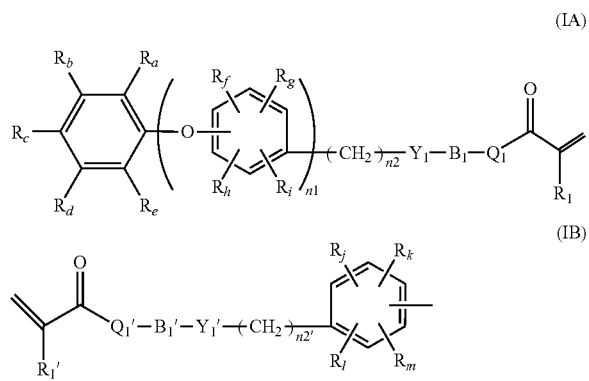

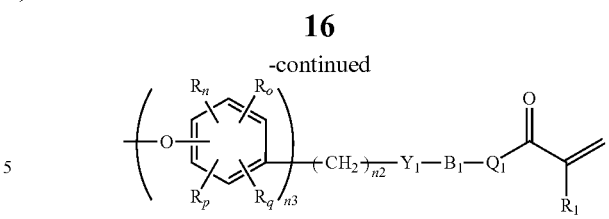

wherein:

$R_1$ and $R_1'$ independently of each other are H or $CH_3$;

$R_a$, $R_b$, $R_c$, $R_d$, $R_e$, $R_f$, $R_g$, $R_h$, $R_i$, $R_j$, $R_k$, $R_l$, $R_m$, $R_n$, $R_o$, $R_p$, and $R_q$ independent of one another are H, $C_1$-$C_{12}$ alkyl, or $C_1$-$C_{12}$ alkoxy;

$B_1$ and $B_1'$ independently of each other are a direct bond, $(CH_2)_{m1}$, or $(OCH_2CH_2)_{m2}$, in which m1 is 2-6 and m2 is 1-10;

$Q_1$ and $Q_1'$ independently of each other are a direct bond, O, NH, or $C(=O)NH(CH_2)_{m3}O$ in which m3 is an integer of 2-6;

n1 is an integer from 1 to 9;

n2 and n2' independently of each other are an integer from 0 to 6;

n3 is an integer from 1 to 100; and $Y_1$ and $Y_1'$ independently of each other are a direct bond, O, S, OC(=O)NH, NHC(=O)NH, or NR' in which R' is H, $C_1$-$C_{10}$ alkyl, $C_6H_5$, or $CH_2C_6H_5$.

2. The device material of claim 1, wherein the device material is characterized by having a refractive index of 1.58 or greater measured at 589 nm and at room temperature in fully hydrated state, a Young's modulus of from about 1 MPa to about 45 MPa, a glass transition temperature of about 30° C. or less, an elongation of at least 110%.

3. The device material of claim 2, wherein the polymerizable composition comprises:

a) from about 40% to about 95% by weight of at least one poly(phenyl ether)-containing monomer of formula (IA) as defined above; and b) from about 1% to about 6% by weight of a poly(ethylene glycol)-containing polymerizable component comprising at least one polymerizable group which is acryloyl (OC(=O)CH=CH_2), methacryloyl (OC(=O)CCH_3=CH_2), acrylamido (NHC(=O)CH=CH_2), methacrylamido (NHC(=O)CCH_3=CH_2), or thiol group.

4. The device material of claim 3, wherein said at least one poly(phenyl ether)-containing monomer is selected from the group consisting of:

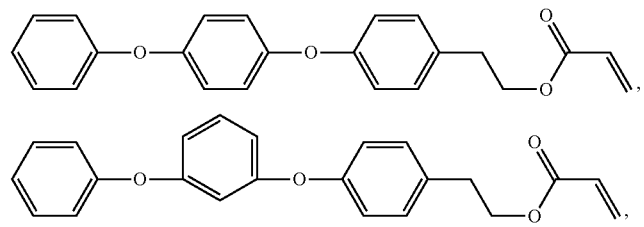

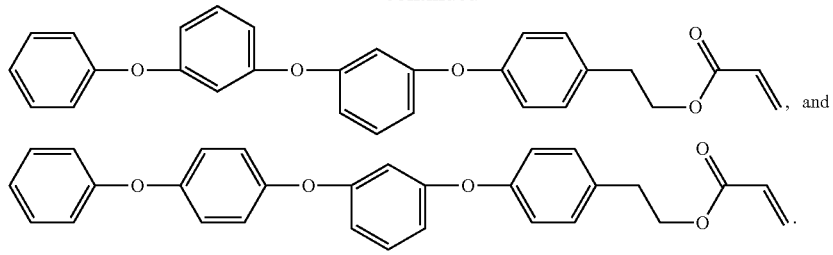
, and

.

5. The device material of claim 4, wherein the poly(ethylene glycol)-containing polymerizable component is represented by formula (II)

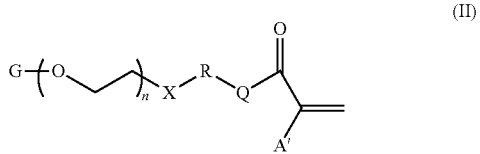

wherein: A' is H or CH$_3$; Q and Q' independently of each other are a direct bond, O, NH, or C(=O)NHCH$_2$CH$_2$O; X and X' independently are a direct bond, O, NH, OC(=O)NH, or NHC(=O)NH; R and R' independently of each other are a direct bond, or (CH$_2$)$_p$; p=1-3; m=2-6; G is H, C$_1$-C$_4$ alkyl, (CH$_2$)$_m$NH$_2$, (CH$_2$)$_m$CO$_2$H, or R'-X'-Q'-C(=O)CA'=CH$_2$; and n=45-225 when G=H, C$_1$-C$_4$ alkyl, (CH$_2$)$_m$NH$_2$, or (CH$_2$)$_m$CO$_2$H; otherwise, n=51-225.

6. The device material of claim 5, wherein in formula (II), X and X' independently of each other are a direct bond or O; R and R' are a direct bond; Q and Q' independently of each other are a direct bond or C(=O)NHCH$_2$CH$_2$O; A' is H or CH$_3$; G is C$_1$-C$_4$ alkyl or R'-X'-Q'-C(=O)CA'=CH$_2$; and n=45-180 when G=C$_1$-C$_4$ alkyl; otherwise, n=51-225.

7. The device material of claim 5, wherein the poly(ethylene glycol)-containing polymerizable component of formula (II) has a number average molecular weight of 2,000-10,000 Daltons.

8. The device material of claim 5, wherein the polymerizable composition for making an ophthalmic device material of the invention further comprises from about 10% to about 45% by weight of one or more aryl acrylic monomers of formula (III)

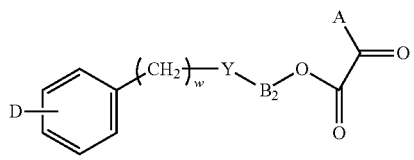

wherein: A is H or CH$_3$; B$_2$ is (CH$_2$)$_m$ or [O(CH$_2$)$_2$]$_z$; m is 2-6; z is 1-10; Y is a direct bond, O, S, or NR', provided that if Y is O, S, or NR', then B is (CH$_2$)$_m$; R' is H, CH$_3$, C$_n$H$_{2n'+1}$, iso-OC$_3$H$_7$, C$_6$H$_5$, or CH$_2$C$_6$H$_5$; n'=1-10; w is 0-6, provided that m+w≤8; and D is H, Cl, Br, C$_1$-C$_4$ alkyl, C$_1$-C$_4$ alkoxy, C$_6$H$_5$, or CH$_2$C$_6$H$_5$.

9. The device material of claim 8, wherein the monomer of formula (III) is selected from the group consisting of: 2-ethylphenoxy acrylate; 2-ethylphenoxy methacrylate; phenyl acrylate; phenyl methacrylate; benzyl acrylate; benzyl methacrylate; 2-phenylethyl acrylate; 2-phenylethyl methacrylate; 3-phenylpropyl acrylate; 3-phenylpropyl methacrylate; 4-phenylbutyl acrylate; 4-phenylbutyl methacrylate; 4-methylphenyl acrylate; 4-methylphenyl methacrylate; 4-methylbenzyl acrylate; 4-methylbenzyl methacrylate; 2-2-methylphenylethyl acrylate; 2,2-methylphenylethyl methacrylate; 2,3-methylphenylethyl acrylate; 2,3-methylphenylethyl methacrylate; 2,4-methylphenylethyl acrylate; 2,4-methylphenylethyl methacrylate; 2-(4-propylphenyl)ethyl acrylate; 2-(4-propylphenyl)ethyl methacrylate; 2-(4-(1-methylethyl)phenyl)ethyl acrylate; 2-(4-(1-methylethyl)phenyl)ethyl methacrylate; 2-(4-methoxyphenyl)ethyl acrylate; 2-(4-methoxyphenyl)ethyl methacrylate; 2-(4-cyclohexylphenyl)ethyl acrylate; 2-(4-cyclohexylphenyl)ethyl methacrylate; 2-(2-chlorophenyl)ethyl acrylate; 2-(2-chlorophenyl)ethyl methacrylate; 2-(3-chlorophenyl)ethyl acrylate; 2-(3-chlorophenyl)ethyl methacrylate; 2-(4-chlorophenyl)ethyl acrylate; 2-(4-chlorophenyl)ethyl methacrylate; 2-(4-bromophenyl)ethyl acrylate; 2-(4-bromophenyl)ethyl methacrylate; 2-(3-phenylphenyl)ethyl acrylate; 2-(3-phenylphenyl)ethyl methacrylate; 2-(4-phenylphenyl)ethyl acrylate; 2-(4-phenylphenyl)ethyl methacrylate; 2-(4-benzylphenyl)ethyl acrylate; 2-(4-benzylphenyl)ethyl methacrylate; 2-(phenylthio)ethyl acrylate; 2-(phenylthio)ethyl methacrylate; 2-benzyloxyethyl acrylate; 3-benzyloxypropyl acrylate; 2-benzyloxyethyl methacrylate; 3-benzyloxypropyl methacrylate; 2-[2-(benzyloxy)ethoxy]ethyl acrylate; 2-[2-(benzyloxy)ethoxy]ethyl methacrylate; and combinations thereof.

10. The device material of claim 5, wherein the polymerizable composition further comprises a poly(phenyl ether)-containing cross-linking agent of formula (IB) and/or a cross-linking agent selected from the group consisting of ethylene glycol dimethacrylate; diethylene glycol dimethacrylate; triethylene glycol dimethacrylate, tetraethylene glycol dimethacrylate, allyl methacrylate; 1,3-propanediol dimethacrylate; 2,3-propanediol dimethacrylate; 1,6-hexanediol dimethacrylate; 1,4-butanediol dimethacrylate; CH$_2$=C(CH$_3$)C(=O)O—(CH$_2$CH$_2$O)$_p$—C(=O)C(CH$_3$)=CH$_2$ where p=1-50; and CH$_2$=C(CH$_3$)C(=O)O(CH$_2$)$_t$O—C(=O)C(CH3)=CH2 where t=3-20; and their corresponding acrylates.

11. The device material of claim 10, wherein the cross-linking agent is selected from the group consisting of: CH$_2$=C(CH$_3$)C(=O)O—(CH$_2$CH$_2$O)$_p$—C(=O)C—(CH$_3$)=CH$_2$ where p is such that the number-average molecular weight is about 400, about 600, or about 1000; ethylene glycol dimethacrylate (EGDMA); diethylene glycol dimethacrylate; triethylene glycol dimethacrylate; triethylene glycol diacrylate; and 1,4-butanediol diacrylate (BDDA).

12. The device material of claim 5, wherein the polymerizable composition further comprises one or more polymerizable components selected from the group consisting of a polymerizable UV-absorber, a polymerizable colored dye, a siloxane monomer, and combinations thereof.

13. The device material of claim 12, wherein the polymerizable composition further comprises a siloxane monomer of formula (IV)

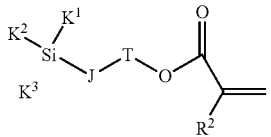

Wherein: $R^2$ is H or $CH_3$; T is a direct bond, $O(CH_2)_b$, or $OCH_2CH(OH)CH_2$; b is 1-3; J is $(CH_2)_z$; and $K^1$, $K^2$, and $K^3$ independently are $CH_3$, $C_6H_5$, or $OSi(CH_3)_3$.

14. An ophthalmic or otorhhinolaryngological device comprising a device material of claim 1.

15. The ophthalmic or otorhhinolaryngological device of claim 14, wherein the ophthalmic or otorhhinolaryngological device is an intraocular lens.

* * * * *